United States Patent [19]

Shipman, Jr. et al.

[11] Patent Number: 4,891,377
[45] Date of Patent: Jan. 2, 1990

[54] TRANSDERMAL DELIVERY OF THE NARCOTIC ANALGESICS ETORPHINE AND ANALOGS

[75] Inventors: Charles Shipman, Jr., Dexter; Mohammad R. Nassiri; Gordon L. Flynn, both of Ann Arbor, all of Mich.

[73] Assignee: Board of Regents Acting for and on behalf of University of Michigan, Ann Arbor, Mich.

[21] Appl. No.: 278,971

[22] Filed: Dec. 2, 1988

[51] Int. Cl.⁴ ............................................. A61K 31/44
[52] U.S. Cl. .................................................... 514/282
[58] Field of Search .......................................... 514/282

[56] References Cited

U.S. PATENT DOCUMENTS

| | | | |
|---|---|---|---|
| 3,763,167 | 10/1973 | Hydro | 260/285 |
| 4,199,576 | 4/1980 | Reller et al. | 514/159 |
| 4,573,995 | 3/1986 | Chen et al. | 514/282 |
| 4,588,580 | 5/1986 | Gale et al. | 424/21 |
| 4,626,539 | 12/1986 | Aungst et al. | 514/282 |
| 4,704,406 | 11/1987 | Stanislaus | 514/570 |

OTHER PUBLICATIONS

Bently and Hardy "New Potent Analgesics in Morphine Series", 1963 p. 220.
Lister "Letters to the Editor", J. Pharm. Pharmacol, 1964, 16, 364, pp. 264–366.
Blane et al., "Letters to the Editor", J. Pharm. Pharmac, 1967, 19, 781, pp. 781–782.
Blane et al., "Action of Etophone", J. Pharmac. Chemother. 1967, 30, pp. 11–22.
Blane et al., "Trial of Etorphine Hydrochloride", Proc. of Brit. Pharmac. Soc. 1970 vol. 39, p. 252.
Lemmon Company M99 Brochure 1984.

Primary Examiner—Stanley J. Friedman
Attorney, Agent, or Firm—Robert B. Stevenson

[57] ABSTRACT

A process for relieving pain and novel topical compositions for transdermal delivery of a narcotic analgesic comprising the application to mammalian skin of an effective amount of a compound of the formula:

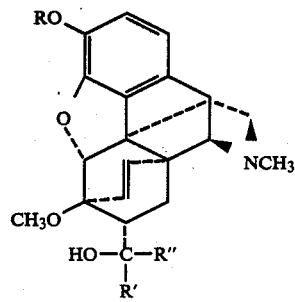

or a pharmacologically acceptable acid addition salt thereof, where R is —$CH_2$,

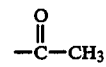

or —H and R' and R" are $C_1$ to $C_6$ hydrocarbons or —H, in association with a topical pharmaceutical carrier selected from the group consisting of ointments, lotions, pastes, jellies, gels, creams, sprays, aerosols and the like.

22 Claims, 7 Drawing Sheets

FIG. 1

EFFECT OF HYDROMORPHONE ON GROWTH OF KB CELLS

TRANSDERMAL DELIVERY OF THE NARCOTIC ANALGESICS ETORPHINE AND ANALOGS

BACKGROUND OF THE INVENTION

1. Field of the Invention

This invention relates to the transdermal delivery of narcotic analgesics. More specifically, the invention relates to pharmaceutical compositions containing as an active ingredient etorphine or an etorphine related analog/derivative in association with a pharmaceutical carrier adapted for topical application to mammalian skin and delivery system for transdermal use of such compositions.

2. Description of the Prior Art

It is generally known and an accepted practice to administer opioid narcotic analgesics such as morphine and morphine related compounds to control chronic pain. Such narcotic analgesics play a prominent role in the control of pain associated with chronic diseases, especially the chronic pain of cancer, and acute pain, especially the acute pain experienced post-operatively. However, such prior art uses of narcotic analgesics are subject to serious problems. In addition to the obvious problem associated with potential abuse and addiction, the oral and parenteral administration of a narcotic analgesic for pain control frequently involve wide swings in the pharmacodynamics of the narcotic drug over each dosing interval. In other words, the peaks and valleys of blood levels of the drug associated with discrete doses leads to patients passing in and out of sedation (euphoria, dysphoria) on the early side and pain on the late side of the dosing interval. Furthermore, analgesic narcotics characteristically have short durations of action, tend to be sedative in pain relieving doses, are inefficiently absorbed orally due to first pass metabolism, tend to depress respiration and tend to be nauseating and/or have other side effects. Surprisingly, very little is reported in the published literature concerning the cytotoxicity of such compounds.

More recently, special interest in the transdermal route of administering narcotics in cancer patients has arisen. In such cases, pain is the most common symptom for which patients seek medical relief and therefore, a more reliable method of delivery and safer route of drug administration to patients are of primary concern. The transdermal delivery of narcotic analgesics, in principle, should have clinical advantages such as (1) it would allow patients to become mobile, (2) it would avoid the necessity of having a sterile syringe, needle, and cleansing of the skin with alcohol or other substance prior to injection as well as avoiding the after pain of injections, (3) it would also avoid the peak and trough phenomenon, and (4) it should reduce the risk of addiction in that a non-euphoric steady state would be maintained rather than the euphoria producing peaks associated with each time the drug is administered parenterally. However, again, very little is known as to the cytotoxicity of narcotic analgesics in transdermal application and in particular, whether or not a reliable and safe transdermal narcotic analgesic therapy exists.

SUMMARY OF THE INVENTION

The present invention provides novel topical compositions containing etorphine or an etorphine related compound (analogs and/or derivatives) as the active analgesic agent as well as transdermal methods and device for therapeutically administering the same. According to the present invention, the permeability coefficients or mass transfer coefficients of the compositions through mammalian skin tissue are established as being sufficient in magnitude to be practical for direct transdermal applications producing time sustained dosage rates consistent with pain suppression and tranquilizing effects over prolonged periods of time. Further, according to the present invention, the compositions for transdermal application are extraordinarily biologically mild relative to cellular growth and viability in that they exhibit virtually no cytotoxicity for neoplastic or normal cells. As such, the present invention provides for safe and reliable transdermal delivery of etorphine and etorphine type narcotic analgesics for the control of pain, particularly the chronic pain associated with cancer and the acute pain frequently experienced post-operatively.

Thus, the present invention provides a topical composition for transdermal delivery of a narcotic analgesic comprising an effective amount of a compound of the formula:

or a pharmacologically acceptable acid addition salt thereof, where R is —CH$_3$, or —H and R' and R" are C1 to C$_6$ hydrocarbons or —H, in association with a topical pharmaceutical carrier selected from the group consisting of ointments, lotions, pastes, jellies, gels, creams, sprays and aerosols.

The method for relieving pain and for tranquilizing according the present invention comprises the application of the above compositions to mammalian skin and in particular, provides for inducing and maintaining analgesia by administering through an area of intact skin, a skin permeable form of a material selected from the group consisting of etorphine and its analgetically effective derivatives at an analgetically effective rate and continuing the administration of said material at said rate for an extended period of time at least sufficient to induce analgesia.

The medical device for the transdermal administration of a material selected from the group consisting of etorphine and its analgetically effective analogs and derivatives at an analgetically effective rate for an extended period of time according the present invention comprises:

(a) reservoir means containing a skin permeable form of said material in an amount sufficient to deliver said material at said analgetically effective rate for said extended period of time; and (b) means for maintaining said reservoir means in material transmitting relationship to intact skin.

It is an object of the present invention to provide an improved method of treating and controlling acute and chronic pain and in particular to alleviate the chronic pain associated with cancer. It is a further object of the present invention to provide for the above control of pain over a sustained period of time by administering a transdermal analgesic containing the extremely potent opioid narcotic etorphine. It is still a further object of the invention to provide such treatment in a manner, such as by use of a patch, that avoids many of the prior art problems associated with the administration of morphine and morphine related drugs. Fulfillment of these objects and the presence and fulfillment of other objects will be apparent upon complete reading of the specification and claims taken in conjunction with the attached drawings.

BRIEF DESCRIPTION OF THE DRAWINGS

FIG. 1 is a plot of cell population as a function of incubation time illustrating the effect of codeine phosphate on the growth of KB cells.

FIG. 2 is a plot of cell population as a function of incubation time illustrating the effect of hydromorphone on the growth of KB cells.

FIG. 3 is a plot of cell population as a function of incubation time illustrating the effect of morphine sulfate on the growth of KB cells.

FIG. 4 is a plot of cell population as a function of incubation time illustrating the effect of etorphine hydrochloride on the growth of KB cells.

FIG. 5 is a plot of cell population as a function of incubation time illustrating the effect of fentanyl on the growth of KB cells.

FIG. 6 is a plot of cell population as a function of incubation time illustrating the effect of sufentanil on the growth of KB cells.

FIG. 7 is a typical plot of cumulative radioactivity of $[^3H]$Etorphine in the receiver cell as a function of time for use in calculating the permeability coefficient.

DESCRIPTION OF THE PREFERRED EMBODIMENTS

In order to more fully appreciate and evaluate the efficacy, reliability and safety associated with the potential transdermal application of any analgesic drug, certain fundamental categorical inquires must be satisfied. First and foremost, the potency of the drug by conventional parenteral and/or oral administration has to be considered relative to the desired analgesic effect and relative to any undesirable side effect. In other words, the analgesic drug must be sufficiently potent to suppress pain, yet be sufficiently free of side effects and clinical complications to warrant therapeutic use. As a general class, the opioid analgesics are known to induce analgesia and/or act as tranquilizers, yet it is also known, for example, that morphine and its analogs vary in potency, efficacy, undesired side effects and clinical complications such as constipation, nausea, vomiting and respiratory depression when the drug is given in excessive dose or adequate doses are administered too frequently. Secondly, in order to be considered effective in transdermal application, both the drug and the skin must survive the passing of the drug through the epidermis/dermisat elevated concentrations. As such, the cytotoxicity of the drug must be considered in that tolerance of skin cells for the drug must be favorable (i.e., necrosis of skin cells at the site of drug application is unacceptable) and the drug cannot be unfavorably biochemically altered as it passes through the skin. In addition to this biological and physicochemical feasibility, the transdermal analgesic must also exhibit favorable pharmacodynamics in that the quantitative rate of delivery of drug transdermally must be consistent with intravenous or subcutaneous dosage requirement relative to a pragmatically acceptable topical surface area. For example, the typical analgesic dosage requirement for morphine of 60 mg or greater per diem when considered relative to the typical skin permeability for opioids rules out the use of morphine as subpotent in transdermal applications. However, since etorphine type analgesics are reported to be 1,000 to 60,000 times more potent than morphine, they cannot be ruled out as subpotent in pragmatic transdermal drug administration schemes.

In order to evaluate the physicochemical feasibility and biological feasibility of the narcotic analgesics according to the present invention in transdermal delivery, the cytotoxicity of a series of seven selected compounds were studied. The activity of etorphine hydrochloride supplied by the Department of Pharmacology, the University of Michigan Medical School and the National Institute of Drug Abuse (Washington, D.C.) was compared to morphine sulfate, codeine phosphate and hydromorphone obtained from the University of Michigan Hospital (Ann Arbor, Mich.), thebaine purchased from Sigma Biochemical Company (St. Louis, Miss.) and fentanyl and sufentanil from Jenssen Pharmaceutica (Piscataway, N.J.). To measure cytotoxicity, three different bioassays were performed using an established line of human cells. The effects of the narcotic analgesics on DNA, RNA and protein synthesis, as more fully explained later, was measured by monitoring the uptake and incorporation of radio labeled thymidine, uridine and amino acids, respectively. Also, the inhibition of cell growth was studied by measuring population doubling times of actively growing cells in the absence and presence of the seven selected compounds. Finally, cloning efficiencies of human cells were determined in the presence of compounds.

Cell cytotoxicity assay measurements using labeled precursors

Cytotoxicity of narcotic analgesics in KB cells was determined in part by measuring inhibition of DNA, RNA and protein synthesis. The KB cells, an established human cell line derived from an epidermal oral carcinoma were routinely grown in minimum essential medium (MEM) with Hanks salts [MEM(H)]supplemented with 5% fetal bovine serum (FBS) purchased from Hyclone Laboratories, Inc. (Logan, Utah). Cells were passaged according to conventional procedures using 0.05% trypsin plus 0.02% ethylenediaminetetraacetic acid (EDTA) in a 4-(2-hydroxyl)-1-piperazineethane-sulfonic acid (HEPES)-buffered salt (HBS) solution, the HEPES was from Calbiochem (La Jolla, Calif.). In order to increase the likelihood of detecting bacterial and/or mixed bacterial and mycoplasmal contamination antibiotics were never employed in the routine passage of cells. Suspension cultures of KB cells were grown an 37° C. in MEM with spinner salts [MEM(S)] ($NaHCO_3$ reduced to 1.9 g/liter) supplemented with 10% calf serum. Suspension grown KB cells had an average population doubling time of 28 hours. They were maintained between $2\times10^5$ and $3 \times 10^5$ cells/ml at a volume of between 250 and 300 ml in hanging bar-type 500ml spinner flasks (Bellco Glass Co., Inc., Vineland, N.J.).

Cells were planted using a Costar Transplate-96 (Costar, Cambridge, Mass.) in 96-well dishes at a concentration of 12,000 cells per well suspended in 200 μl of medium. After incubation for 20-24 hours at 37° C. in a humidified atmosphere of 4% $CO_2$-96% air, 150 μl of medium was removed per well. One hundred μl of medium containing drugs in twice their final concentrations were added to each well using a Titertek Multichannel pipette (Flow, Laboratories nc., McLean, Va.). Fifty μl of medium containing radioactive precursors was then added to each well to give final concentrations of 2 μCi/ml of [$^3$H]dThd and 3μCi/ml of [$^3$H]Urd or $^3$H-amino acids using [Methyl-$^3$H]thymidine (40Ci/mmole),[5-$^3$H]Uridine (22Ci/mmole), and $^3$H-L-amino acid mixture (273 mCi/mg) purchased from ICN Biochemicals, Inc. (Irvine, Ca.). In all experiments [$^3$H]dThd and [$^3$H]Urd were diluted with unlabeled dThd and Urd (final concentration of 2 μM) to ensure that sufficient precursor was available for uptake beyond 16 hours. Addition of drugs and labeled precursors were in triplicates, and plates were incubated for an additional 16-24 hours. Logarithmic cell growth occurred during this time with continual uptake of labeled precursors. At the end of the incubation period, cells were harvested from each well using a Skatron Cell Harvester (Skatron, Inc., Sterling, Va.). Cultures from individual wells were harvested onto filter paper and washed free of unincorporated label with sequential washes with 5% trichloroacetic acid and water using the Skatron unit. Filters were dried, circles from individual cultures punched from the filter mat and placed into mini-vials. Liquid scintillation solution was added and radioactivity was determined in a Beckman model LS 8100 liquid scintillation spectrometer. The resulting values for 50% inhibitory concentration ($IC_{50}$) are presented in TABLE I.

TABLE I

Effect of narcotic analgesics on incorporation of labeled precursors into DNA, RNA, and protein.

| | | $IC_{50}$ (mM)[a] | | |
|---|---|---|---|---|
| Group | Drug | DNA | RNA | Protein |
| I | Codeine | >1.0[b] | >1.0[b] | >1.0[b] |
| | Hydromorphone | >1.0[b] | >1.0[b] | >1.0[b] |
| | Morphine | 2.50 | 4.21 | 3.42 |
| | Thebaine | >1.0[b] | >1.0[b] | >1.0[b] |
| | Etorphine | >1.0[b] | >1.0[b] | 4.15 |
| II | Fentanyl[c] | 0.47 | 0.25 | 0.30 |
| | | (0.16-15.00) | (0.09-4.3) | (0.15-0.93) |
| | Sufentanil[c] | 0.08 | 0.20 | 0.11 |
| | | (0.02-0.56) | (0.06-4.0) | (0.04-2.0) |

[a]Calculated from the regression lines of the dose-response relationships against log drug concentration.
[b]Less than 15% inhibition observed at highest concentration (1.0 mM) tested.
[c]95% confidence interval given in parenthesis.

Concentration of narcotics were tested in the range of 10μM to 1.0 to 10.0 mM for the incubation periods of 20-24 hours. As seen in the top five narcotics (codeine through etorphine, hereinafter referred to as group I), the $IC_{50}$ values for nucleic acids and protein were all >1.0 mM. In addition, by examining the drug treated cells using microscope, neither anatomical damage of the cells nor any slowness of the cell growth was noted.

In contrast, the final two narcotics (fentanyl and sufentanil, hereinafter referred to as group II) had inhibitory effects on the incorporation of labeled precursors into cellular DNA, RNA and protein. The effect of sufentanil was found to be in a greater extent than its congener fentanyl. Table I displays the IC50 values calculated as 95% confidence interval given in parenthesis for fentanyl and sufentanil. The concentrations tested in group II narcotics were from 10.0 to 1000.0 μM range for the incubation periods of 20-24 hours. The effects of group II narcotics show a consistency of inhibition to a similar extent for both nucleic acids and proteins. Sufentanil at 1.0 mM concentration inhibited the incorporation of more than 98% of tritiated thymidine, uridine and amino acids, whereas the effects with fentanylat the concentration indicated above was seen to lesser extent resulting to 37,32 and 25 percent inhibition of labeled precursors into cellular DNA,RNA and protein respectively. When the inhibitory concentration values in group II were averaged to give a general indication of cytotoxicity, the effect of sufentanil was 2.6 fold greater than the effect with fentanyl.

Cell Growth Curves

KB cells were planted in 6-well plastic tissue culture dishes (Costar, Cambridge, Mass.) at a concentration of $1 \times 10^5$ cells per well and incubated for 20 to 24 hours, during which time cells attached to the substrate. Medium was decanted, the cell sheet was rinsed once with HBS, and fresh growth medium containing various concentrations of drugs was added. After additional periods of incubation at 37° C., medium was removed and cells were harvested with 0.05% trypsin-0.02% EDTA in HBS.

Total cell counts were made with a model Z; Coulter Counter (Coulter Electronics, Inc., Hialeah, Fla.) equipped with a 100-μm orifice. Viable counts were determined by means of trypan blue dye exclusion. Population doubling times were calculated by means of a least squares program fitting the exponential portion of the growth curve. The numbers of cells at each time point and concentration were plotted against time to contrast growth curves. FIGS. 1 through 6 present these data plots.

Treatment of KB cells in culture for up to 72 hours of incubation periods with various concentrations of group I narcotics resulted in no decrease or a minimal decrease in cell growth (see FIGS. 1-4). Contrary to group I, group II narcotics (see FIGS. 5 and 6) showed significant cell growth suppression. PDT of KB cells treated with fentanyl and to a greater extent with sufentanil was prolonged for the incubation periods of 24 hours. It can be seen from FIG. 5 that the suppression of cell growth occurred at levels of 100 μM of fentanyl. Sufentanil had a typical cell growth curve effect. Suppression of cell growth occurred for as low as 10 μM, and at 100 μM of sufentanil, inhibition of cell growth was dramatic (see FIG. 6).

Cloning Efficiencies

The relative ability of KB cells to clone in media in the presence of the various concentrations of narcotics and in their absence in the media was examined. The results for the selected narcotics are statistically present in TABLE II (as number of experiments, n, arithmetic mean, x, and standard deviation, S.D.).

The 50% inhibitory doses were compared between group I and II by using Scheff's method of multiple comparison. Among these two groups, morphine had the highest $IC_{50}$ value of 1.86 μM, and in contrast sufentanil had the lowest $IC_{50}$ value of 0.1 μM. However, by examining Table II: (1) the 50% reductions in number of clones were not significantly different between group II narcotics and codeine, hydromorphone, and thebaine, (2) group II significantly differed with etorphine (p>0.05), and (3) the results for morphine was also found to be statistically different between other members of group I narcotics as well as group II.

TABLE II

Effect of narcotic analgesics on the relative plating efficiency of KB cells[a].

| Drug | n[b] | X[c] | S.D. |
|---|---|---|---|
| { { Sufentanil | 3 | 0.10 | ±0.001 |
| Fentanyl | 3 | 0.20 | ±0.038 |
| { Codeine PO$_4$ | 3 | 0.34 | ±0.171 |
| Hydromorphone | 3 | 0.52 | ±0.286 |
| Thebaine | 3 | 0.74 | ±0.097 |
| Etorphine HCl | 2 | 0.98 | ±0.061 |
| Morphine SO$_4$ | 2 | 1.86 | ±0.348 |

[a]Approximately 500 to 650 cells were seeded per dish. After incubation for 12 to 14 days at 37° C., clones were fixed and stained with crystal violet. Clones greater than 1 mm in diameter were scored.
[b]Number of experiments.
[c]Arithmatic mean of concentration of drug required to produce a 50% reduction in the number of clones developing in the absence of the drug.
*Arithmatic means within bracketed groups were not significantly different (p > 0.05) using Scheff's method of multiple comparisons.

In reviewing the above cell cytotoxicity assays, cell growth curves, and cloning efficiency, several conclusions can be made. The experiments using radioactive precursors to measure the rate of DNA, RNA. and protein synthesis revealed that group I narcotics did not exert any significant cytotoxic effects on KB cells for the concentrations that were examined in the study. In contrast, the group II narcotics (fentanyl and sufentanil) appear to be markedly more cytotoxic. Similarly, the results of the cell growth curves indicate that KB cells grow in the presence of group I narcotics with little or no suppression. Again, when the KB cell cultures were subjected to group II narcotics, the results were quite different. Inhibition of cell growth occurred at 100 μM for fentanyl and started at 32 μM for sufentanil. In contrast, the highest drug concentration used for group I was 320 μM for 72 hours of incubation with no cytotoxic effect. In a manner analogous to the KB cell growth curve measurements, diploid cell cultures of human foreskin fibroblasts were tested for narcotic inhibition of cell growth with no significant difference relative to that observed with the KB cells being recorded. This in combination with the radioactive isotope measurements clearly indicate minimal cytotoxicity of etorphine for both neoplastic and normal human cells.

Cloning efficiency is a sensitive method of examining cell growth and viability in the presence of a drug. In this case, the clone assay provided additional information on the validity of the above conclusions relative to cell biosynthesis and growth. Cloning efficiency experiments using group II narcotics with KB cells showed a 15% reduction at 100 μM for fentanyl and 30% reduction for sufentanil at the same concentration described. When fentanyl and sufentanil tested at the highest concentration (1000 μM), nearly 100% inhibition of clones was noted. Furthermore, since the incubation of drugs in cloning efficiency assays followed a period of 12–14 days, the pH of the cell growth media for all drugs tested, was measured at the first and last day of incubation period. No significant drop in pH in the presence or absence of drugs was found. It has been previously reported that highly lipophilic drugs like fentanyl are sequestered in human lungs and therefore bound to lung tissue. The extent of fentanyl accumulation was concluded to exceed by far that seen in animals. Thus, it is likely that the transport of fentanyl or its congener sufentanil by human lungs may facilitate and give rise to potential cytotoxic activity in lung tissue. For that matter, in chronic illness, those patients who are under long term treatment with analgesic narcotics such as sufentanil may suffer the chemical effect. Thus, again, the cloning efficiencies indicate that etorphine, despite its extraordinary analgesic potency, is remarkably inactive in cell culture.

In order to evaluate the pharmacodynamic suitability of the narcotic analgesics according to the present invention in transdermal delivery, the permeability coefficients through human epidermal membranes and selected mammalian epidermal membranes were measured. The studies were directed to assessing how much of a given drug could be delivered through the skin.

As previously indicated, a primary consideration and concern of any transdermal system is the adequacy of the drug delivery. To a degree, this can be controlled by adjusting the transdermal patch's area, but there are pragmatic limits as to surface area of a patch. As such, skin permeability relative to dose is the primary issue. Thus, the 60 mg per diem dosage for morphine rules out morphine, while mg dosages might allow for transdermal use and μg dosages typical of etorphine and derivatives is encouraging.

Mass Transfer Coefficient of Etorphine Hydrochloride

The in vitro studies to quantitatively measure the permeability coefficient of etorphine hydrochloride through skin tissue involved mounting excised skin between two reservoirs which comprise the essential elements of a diffusion cell. The source of mammalian skin tissue employed was from hairless mice (SKH-hr-1 strain supplied by Skin Cancer Hospital, Philadelphia, Pa.), 120 to 150 days old. The abdominal and dorsal skin of the mouse was blocked out into six square sections. Each section was excised with surgical scissors, wetted with Tris buffer (14.4 mM, pH=7.4) and then the adhering fat and other visceral debris were removed carefully from the undersurface with scalpel.

The skin sections were mounted carefully between the half-cells of the diffusion cell (SIDE-BI-SIDE DC-100B, Crown Glass Co., Inc., Somerville, N.J.) each of 3 ml capacity and individually jacketed with circulating water maintained at 37° C. Each chamber had a circular opening (0.64 cm$^2$ in area) for diffusion. Stirring of the media within the chamber was achieved by externally driven magnetic stirring bars placed in circular depressions of the chambers near the opening. Each chamber was fitted with a glass-stoppered port on top for addition or removal of medium within the chamber.

After the receiver compartments were filled with 2.8 ml of Tris buffer (pH=7.4), 2.8 ml of [$^3$H]Etorphine solution (radioactivity=0.125μci/ml) was added to the donor compartment. The cell contents were stirred with magnetic bars at a rate of 150 rpm. At predetermined times, 1 ml samples were withdrawn from the receiver compartment and transferred to scintillation vials for determination of radioactivity. To maintain the same volume on the receiver compartment, 1 ml of Tris buffer was added after each sample withdrawn.

Figure 1:
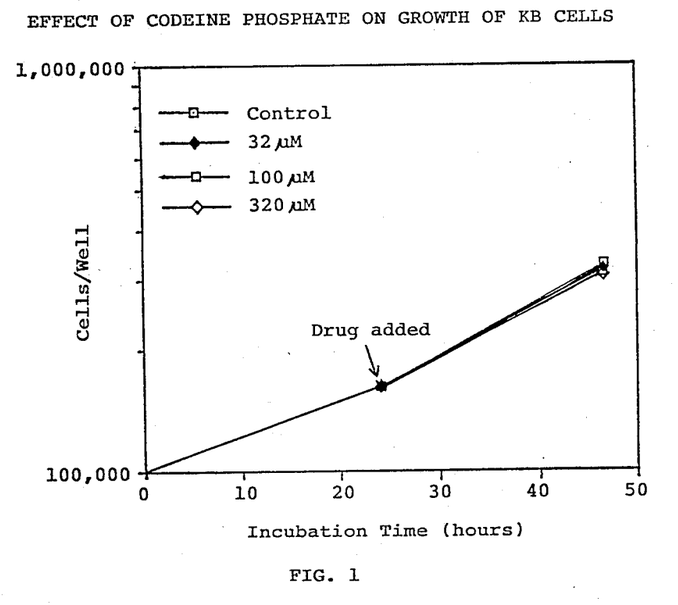
Figure 2:
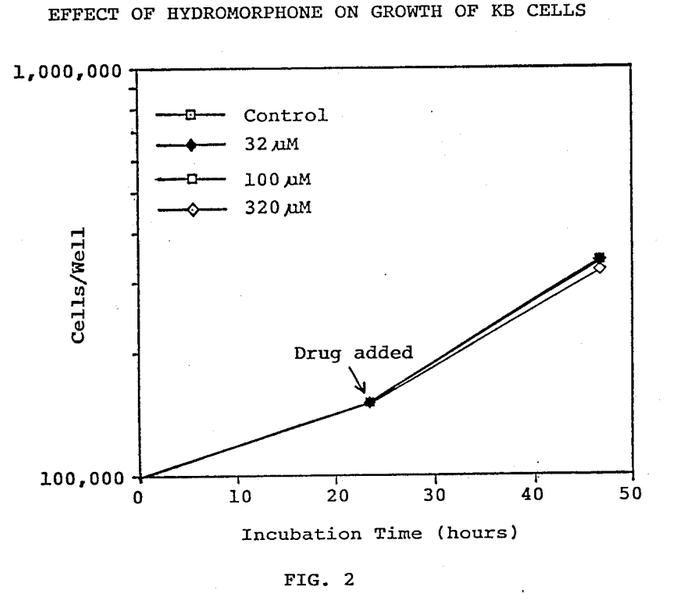
Figure 3:
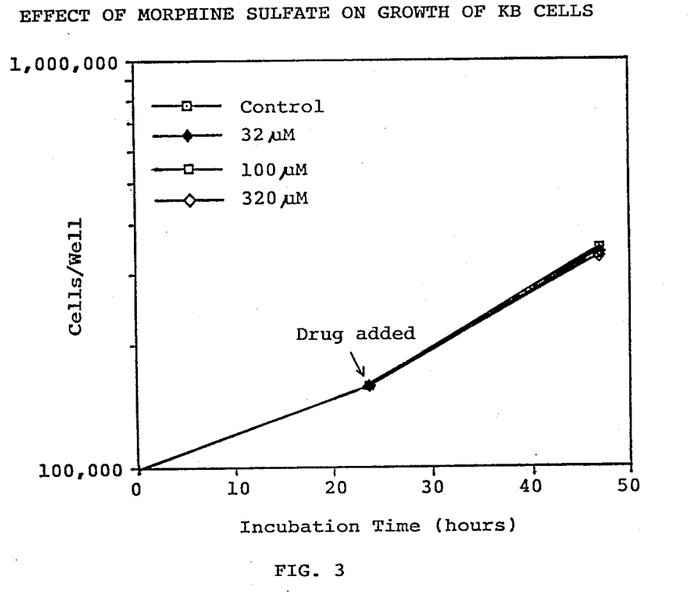
Figure 4:
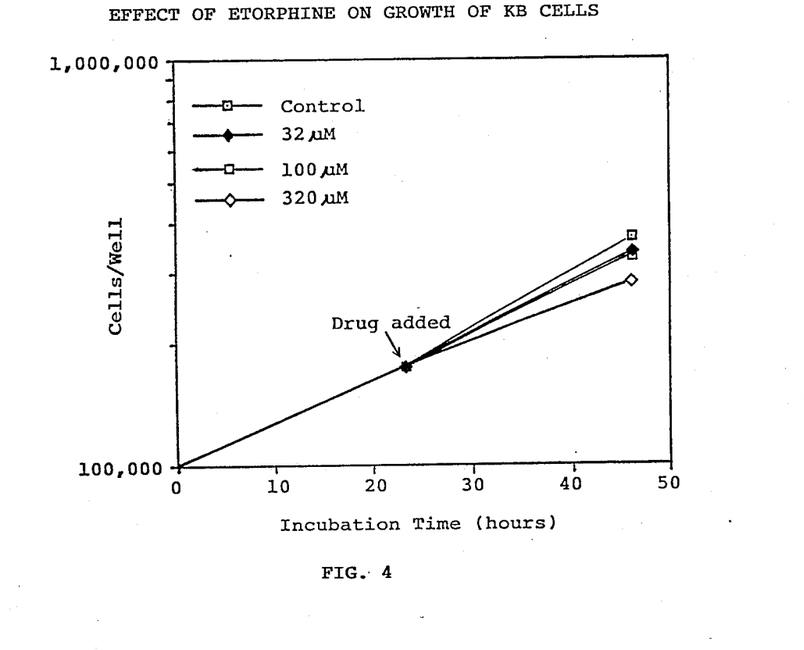
Figure 5:
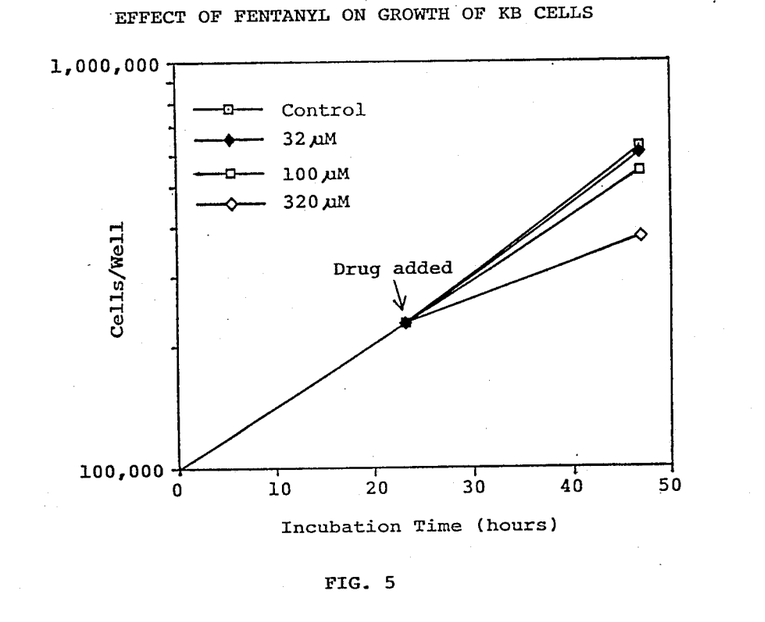
Figure 6:
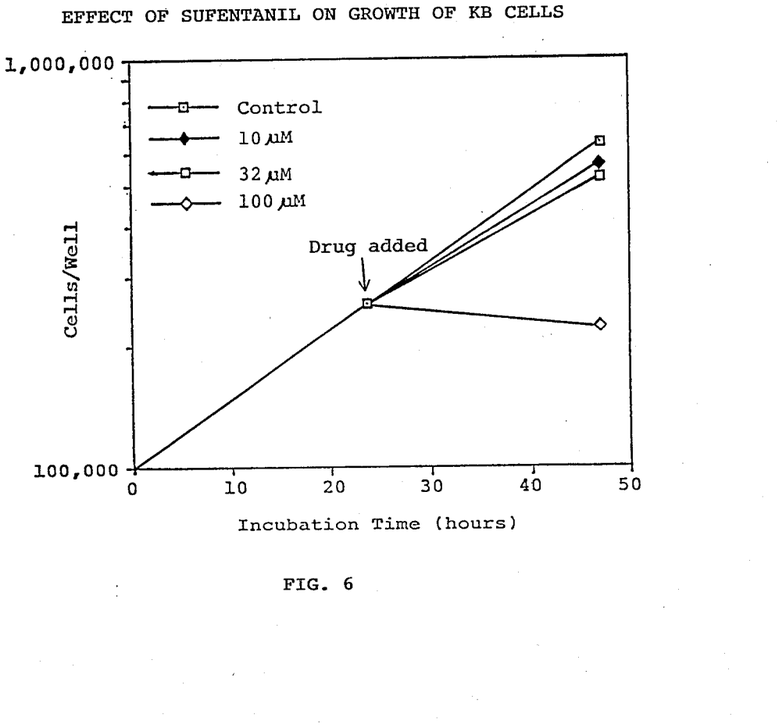
Figure 7:
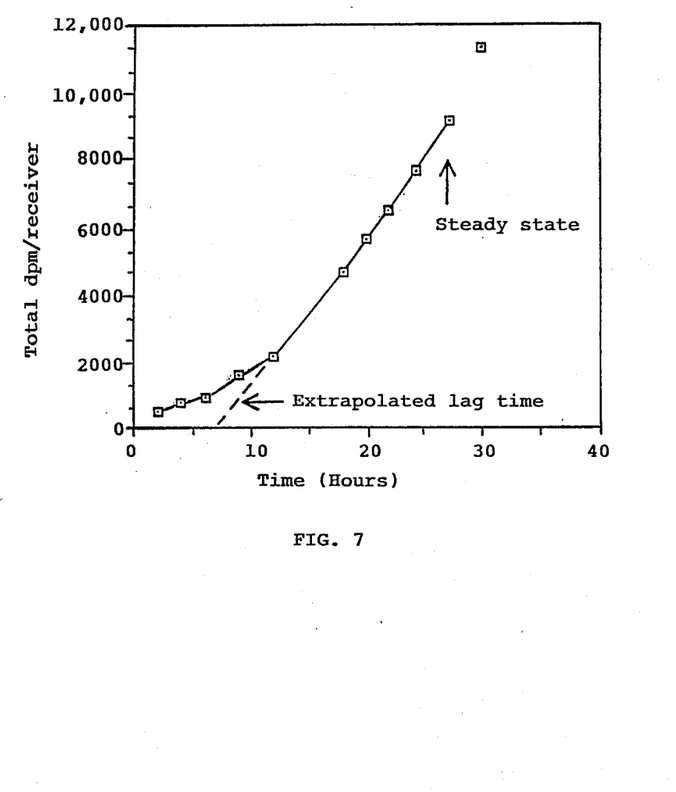

The data were plotted as cumulative dpm collected in the receiver compartment as a function of time, see FIG. 7. The permeability coefficient for a given experiment was calculated from Flick's second law:

$$dM/dt = J_T = P \cdot A \cdot \Delta C$$

Where, $dM = V \cdot dC$; $J_T$ is the total pseudo-steady state flux (μg/ml) across the skin; P is the permeability coefficient (cm/h); A is the diffusional area which was 0.64 cm² in the present study; $_\Delta C$ is the concentration differential across the membrane, which was taken to be the donor phase concentration (dpm/ml); dM/dt is the steady-state slope in terms of dpm/h; V is the diffusion cell volume and C is the receptor concentration (dpm/ml).

The statistical analyses of data obtained were performed by Student's t-test and the results are summarized in TABLE III.

TABLE III

| | Permeability Coefficient of Etorphine | |
|---|---|---|
| Drug Etorphine | J (dpm/h/cm²) | P (cm/h) |
| Hairless mice | 885.30 | $4.94 \times 10^{-3}$ |

The advantages and benefits of using the transdermal application of narcotic analgesics based on etorphine and etorphine analogs according to the present invention are considered numerous and significant. Because of the extraordinary potency of etorphine, typically measured in terms of thousands of times more potent than morphine, the method and composition of the present invention typically do not cause vomiting or nausea at equivalent analgesic dosage rates (i.e., thousand fold lower absolute dosage rates). These lower absolute dosage rates in combination with the discovery that etorphine is biologically unoffending showing little direct effect on cells (protein synthesis, DNA and RNA synthesis and cell replication) reduces the potential to induce irritant response in the skin or other detrimental side effects. The observed lack of cytotoxic effects on both neoplastic and normal cells indicates that the compositions according to the present invention are particularly useful in control of pain in cancer patients and/or other chronic illness. The fact that transdermal application of the analgesic can be administered without the conscious assistance of the patient and bypasses the pain associated in intravenous or subcutaneous injections or the like, suggest that the method according to the present invention is particularly useful for alleviating acute pain and, in particular, acute pain experienced postoperatively. And most importantly, the permeability coefficients or, more specifically, the mass transfer coefficients establish that the compositions according to the present invention are uniquely suited for transdermal applications.

The actual administration or use of the transdermal analgesic compositions according to the present invention can be in any conventional form and by any of the methods generally known in the art. Thus, the active narcotic analgesic compound (i.e., etorphine or etorphine analog, including derivatives and/or mixtures thereof) is to be used in association with any pharmaceutical carrier such as, for example, but not limited thereto, any solution, ointment, lotion, paste, jelly, gel, cream, spray or aerosol as generally known in the art. As such, the narcotic analgesic in association with the pharmaceutical carrier can be used directly as a topical composition or used in combination with, for example, but not limited thereto, patches, gauze, compresses, or the like, again, as generally known in the art. In particular, the transdermal analgesic compositions can be administered in the form of a patch wherein the active etorphine agent is present in a polymeric reservoir material.

Having thus described the invention with a certain degree of particularity, it is to be understood that the invention is not limited to the embodiments as set forth hereinfor purposes of exemplification, but is to be limited only by the scope of the attached claims, including a full range of equivalents to which each element thereof is entitled.

We claim:

1. A process for relieving pain comprising the application to mammalian skin of an effective amount of a compound of the formula:

or a pharmacologically acceptable acid addition salt thereof, where R is —CH₂, —C—CH₃ or —H and R' and R" are C₁ to C₆ hydrocarbons or —H, in association with a topical pharmaceutical carrier selected from the group consisting of solutions, ointments, lotions, pastes, jellies, sprays and aerosols.

2. A process of claim 1 wherein said compound is etorphine.

3. A process of claim I wherein said compound is etorphine hydrochloride.

4. A process of claim 1 wherein R is —H, R, is —CH₃ and R" is

5. A process of claim 1 wherein R is

R' is —CJ₃ and R" CH₂, —CH₂, —CH₃.

6. A process of claim 4 wherein the compound is the hydrochloride addition salt.

7. A process of claim 5 wherein the compound is the hydrochloride addition salt.

8. A process for tranquilizing a mammal comprising the application to mammalian skin of an effective amount of a compound of the formula:

or a pharmacologically acceptable acid addition salt thereof, where R is —CH$_2$, —C—CH$_3$ or —H and R and R" are C$_1$ to C$_6$ hydrocarbons or —H, in associated with a topical pharmaceutical carrier selected from the group consisting of solutions, ointments, lotions, pastes, jellies, sprays and aerosols.

9. A process of claim 8 wherein said compound is etorphine.

10. A process of claim 8 wherein said compound is etorphine hydrochloride.

11. A process of claim 8 wherein R is —H, R, is —CH$_3$ and R" is

12. A process of claim 8 wherein R is

R' is —CH$_3$ and R" is —CH$_2$, —CH$_2$, —CH$_3$.

13. A process of claim 11 wherein the compound is the hydrochloride addition salt.

14. A process of claim 12 wherein the compound is the hydrochloride addition salt.

15. A process for inducing and maintaining analgesia which comprises administering through an area of intact skin, a skin permeable form of a material selected from the group consisting of etorphine and its analgetically effective derivatives at an analgetically effective rate and continuing the administration of said material at said rate for an extended period of time at least sufficient to induce analgesia.

16. A topical composition for transdermal delivery of a narcotic analgesic comprising an effective amount of a compound of the formula:

or a pharmacologically acceptable acid addition salt thereof, where R is —CH$_3$, or —H and R' and R" are C1 to C$_6$ hydrocarbons or —H, in association with a topical pharmaceutical carrier selected from the group consisting of ointments, lotions, pastes, jellies, gels, creams, sprays and aerosols.

17. A topical composition of claim 16 wherein said compound is etorphine.

18. A topical composition of claim 16 wherein said compound is etorphine hydrochloride.

19. A topical composition of claim 16 wherein R is —H, R, is —CH$_3$ and R" is

20. A topical composition of claim 16 wherein R is

R' is —CH$_3$ and R" is —CH$_2$—CH$_2$—CH$_3$.

21. A topical composition of claim 19 wherein the compound is the hydrochloride addition salt.

22. A topical composition of claim 20 wherein the compound is the hydrochloride addition salt.

* * * * *

UNITED STATES PATENT AND TRADEMARK OFFICE
CERTIFICATE OF CORRECTION

PATENT NO. : 4,891,377

DATED : 01/02/90

INVENTOR(S) : Shipman et al.

It is certified that error appears in the above—identified patent and that said Letters Patent is hereby corrected as shown below:

Column 1, lines 1-5, insert the following:

--The U.S. Government has a paid-up license in this invention and the right in limited circumstances to require the patent owner to license others on reasonable terms as provided for by the terms of contract No. DA 04061 awarded by the National Institutes of Health.--

Signed and Sealed this

Twenty-ninth Day of December, 1992

Attest:

DOUGLAS B. COMER

*Attesting Officer*   *Acting Commissioner of Patents and Trademarks*